United States Patent
Giuseppone et al.

(10) Patent No.: US 9,849,437 B2
(45) Date of Patent: Dec. 26, 2017

(54) ELECTRIC CONDUCTION THROUGH SUPRAMOLECULAR ASSEMBLIES OF TRIARYLAMINES

(71) Applicants: CENTRE NATIONAL DE LA RECHERCHE SCIENTIFIQUE (C.N.R.S), Paris (FR); Université de Strasbourg, Strasbourg (FR)

(72) Inventors: Nicolas Giuseppone, Strasbourg (FR); Jean-François Dayen, Strasbourg (FR); Vina Faramarzi, Strasbourg (FR); Emilie Moulin, Hangenbieten (FR); Frederic Niess, Strasbourg (FR); Bernard Doudin, Strasbourg (FR)

(73) Assignees: CENTRE NATIONAL DE LA RECHERCHE SCIENTIFIQUE (C.N.R.S.), Paris (FR); UNIVERSITE DE STRASBOURG, Strasbourg (FR)

( * ) Notice: Subject to any disclaimer, the term of this patent is extended or adjusted under 35 U.S.C. 154(b) by 276 days.

(21) Appl. No.: 14/690,938

(22) Filed: Apr. 20, 2015

(65) Prior Publication Data
US 2015/0298092 A1 Oct. 22, 2015

Related U.S. Application Data

(60) Division of application No. 13/421,656, filed on Mar. 15, 2012, now Pat. No. 9,028,722, which is a (Continued)

(30) Foreign Application Priority Data

Oct. 29, 2010 (FR) .................................. 10 58954

(51) Int. Cl.
*H01B 1/12* (2006.01)
*B01J 19/08* (2006.01)
(Continued)

(52) U.S. Cl.
CPC .......... *B01J 19/087* (2013.01); *C07C 233/43* (2013.01); *H01B 1/12* (2013.01);
(Continued)

(58) Field of Classification Search
CPC .................. B01J 19/087; C07C 233/43; H01L 21/76838; H01L 51/0021; H01L 51/0059;
(Continued)

(56) References Cited

U.S. PATENT DOCUMENTS

| 3,180,730 A | 4/1965 | Klupfel et al. |
| 7,042,755 B1 * | 5/2006 | Bocian .................. B82Y 10/00 365/151 |

(Continued)

FOREIGN PATENT DOCUMENTS

| EP | 0 924 724 | 6/1999 |
| JP | 11-183940 | 7/1999 |

OTHER PUBLICATIONS

Yasuda, et al., "4,4',4"-Tris)stearoylamino)triphenylamine as a Novel Material for Functional Material Gels", Adv. Mater. 8,9, pp. 740-741.*

(Continued)

*Primary Examiner* — Mark Kopec
*Assistant Examiner* — Jaison Thomas
(74) *Attorney, Agent, or Firm* — Stephen J. Weyer, Esq.; Stites & Harbison, PLLC (57) ABSTRACT

A method is provided for modifying a surface of a solid conducting material, which includes applying a potential difference between this surface and a surface of another conducting solid material positioned facing it, and wherein, simultaneously, the surface (S) is put into contact with a liquid medium comprising in solution triarylamines (I):

(Continued)

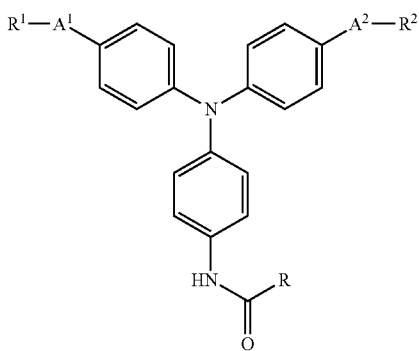

while subjecting these triarylamines (I) to electromagnetic radiation, at least partly converting them at into triarylammonium radicals. Also provided is a conducting device which includes two conducting metal materials, the surfaces of which, (S) and (S') respectively, are electrically interconnected through an organic material comprising conducting fibrillar organic supramolecular species comprising an association of triarylamines of formula (I).

24 Claims, 4 Drawing Sheets

Related U.S. Application Data continuation-in-part of application No. 13/284,104, filed on Oct. 28, 2011, now abandoned, which is a continuation of application No. PCT/FR2011/052529, filed on Oct. 28, 2011.

(60) Provisional application No. 61/418,645, filed on Dec. 1, 2010.

(51) Int. Cl.
- H01L 51/00 (2006.01)
- C07C 233/43 (2006.01)
- H01L 21/768 (2006.01)
- H01L 51/05 (2006.01)

(52) U.S. Cl.
CPC .... H01L 21/76838 (2013.01); H01L 51/0021 (2013.01); H01L 51/0059 (2013.01); H01L 51/0076 (2013.01); H01L 51/0545 (2013.01); Y02E 10/549 (2013.01)

(58) Field of Classification Search
CPC   H01L 51/0076; H01L 51/0545; Y02E 10/549
See application file for complete search history.

(56) References Cited

U.S. PATENT DOCUMENTS

| | | | |
|---|---|---|---|
| 2010/0224867 A1* | 9/2010 | Heuft | B82Y 10/00 257/40 |
| 2011/0101324 A1 | 5/2011 | Masui | |
| 2012/0040282 A1* | 2/2012 | Heuft | G03G 5/0589 430/56 |

OTHER PUBLICATIONS

Notice of Reasons for Rejections dated Aug. 3, 2015 in corresponding Japanese Application No. 2013-535498.

* cited by examiner

ELECTRIC CONDUCTION THROUGH SUPRAMOLECULAR ASSEMBLIES OF TRIARYLAMINES

CROSS REFERENCE TO RELATED APPLICATIONS

This application is a divisional of application Ser. No. 13/421,656, filed Mar. 15, 2012, which is both a continuation of PCT/FR2011/052529, filed Oct. 28, 2011 and a continuation-in-part of application Ser. No. 13/284,104, filed Oct. 28, 2011, which, in turn claims benefit of U.S. Provisional Application No. 61/418,645, filed Dec. 1, 2010, all hereby incorporated by reference.

The present invention relates to the field of electric connection of conducting solid elements separated from each other by small distances, typically of the order of a few tens to a few hundred nanometers, for example conducting solid elements of the type of those applied in electronic and optoelectronic devices, such as light emitting diodes (LEDs and OLEDs), field effect transistors (FETs and OFETs) and photovoltaic devices such as solar cells. The invention according to a particular aspect for example relates to the manufacturing or repairing of electronic circuits (notably printed circuits) where an electric connection has to be established between components for example after having been broken.

To this day, in order to make an electric connection of the aforementioned type, between conducting solid elements separated by small distances, various methods have been proposed which generally prove to be unsatisfactory or limited.

Thus, deposition of metal powders between the conductors to be connected has for example been contemplated. The use of a metal powder of this type generally leads to an electric connection, but generally proves to be relatively difficult to localize accurately, which may lead to undesired connections between other electric conductors than those which are desirably interconnected. Further, the efficiency of the electric connection obtained with a metal powder often proves to be rather poor. Indeed, schematically, powders lead to point-like contacts with the conductors to be connected, which does not induce an optimum electric connection. More generally, the use of metals for making electronic devices generally requires complicated and/or expensive shaping steps and generally leads to rigid devices.

Alternatively, for manufacturing electronic devices, the use of conducting polymers has been proposed, which are typically deposited between conductors to be connected within a solvent which is then evaporated. Some of the proposed polymers within this scope prove to be relatively interesting for connecting specific metal conductor elements, notably insofar that with them it is possible to obtain more flexible devices than those obtained with metals, and with generally lower costs. However, there again, when it is desired to connect two conducting solids with a polymer, it is often difficult to confine the deposit of this polymer to a well-delimited area. Further, when a conducting polymer leads to interesting results with a given metal conductor, these results cannot be generally transposed to other metal conductors. Indeed, the efficiency of the electric connection made with an organic conducting polymer most often depends on the adequacy of the valence bands and adsorption bands of the polymer and of the metal conductor to which it is connected.

Further, organic conducting polymers have the drawback of having a behavior of non-ohmic conductors. Another negative aspect related to the use of conducting organic polymers is that they often contain metal ions as dopants, which may have a non negligible impact in terms of toxicity and of detrimental repercussions on the environment, which is an obstacle to their use on an industrial scale.

Another possibility for connecting two electrodes by means of an organic conductor is to accurately deposit metal carbon nanotubes. This actually has very low interface resistances and an ohmic behavior with metal type conduction. However, the difficulty in insulating and positioning these nanotubes on metal contacts again makes this method difficult to apply and with a high cost.

An object of the present invention is to provide a method which i.a. allows electric connection of two conducting solid elements, in an accurate, simple, repeatable and efficient way, and this preferably by avoiding the drawbacks of the aforementioned methods, notably by ensuring between both conductors an efficient conduction of the ohmic type.

For this purpose, the present invention proposes a novel method, which gives access to the deposition of conducting organic fibrillar structures at the surface (S) of a solid conducting material, which allows i.a. the connection of this thereby modified surface (S) with a surface (S') of another conducting solid placed facing the surface bearing the fibrillar structures, when this other surface (S') is at a sufficiently small distance so that the fibrillar structures may form a connection between both surfaces (S) and (S') facing each other.

More specifically, according to a first aspect, the object of the present invention is a method for modifying a surface (S) of a solid conducting material which comprises a step (E) in which a generally negative potential difference is applied between said surface (S) and a surface (S') of another conducting solid material positioned facing said surface (S), simultaneously with the contacting of said surface (S) with a liquid medium comprising in solution triarylamines fitting the formula (I) hereafter:

wherein:
  each of the groups -$A^1$- and -$A^2$-, either identical or different (and preferably identical), designates a simple covalent bond or else a group —O— or —S—, —NH—, NH(C=O), or —$NR^3$—, and preferably a group —O—;
  each of the groups $R^1$, $R^2$ and $R^3$, either identical or different ($R^1$ and $R^2$ being preferably identical), represents:
  an aromatic group, preferably a benzyl group;

or
a (preferably linear) hydrocarbon chain comprising from 4 to 30, for example 5 to 20 carbon atoms, preferably an advantageously linear fatty chain, notably an alkyl group;
or
a polyethylene glycol chain;
and
R is a terminating group, which preferably is a linear or branched hydrocarbon chain, advantageously comprising from 1 to 10 carbon atoms, optionally halogenated and optionally interrupted with one or several heteroatoms selected from N, O or S,
R more preferably being an alkyl group, optionally halogenated, preferably comprising from 1 to 8 carbon atoms, while subjecting the triarylamines (1) to electromagnetic radiation or to chemical or electrochemical oxidation, suitable for converting them at least partly into triarylammonium radicals, this irradiation may typically be achieved with sunlight in a chlorinated solvent (dichloromethane, chloroform, tetrachloroethane, dichlorobenzene, etc).

With the work which was carried out by the inventors within the scope of the present invention, it was now possible to show that the application of step (E) as defined above gives the possibility of obtaining in an extremely simple and rapid way, a deposit of conducting organic species, with a fibrillar shape (i.e. globally having the morphology of a small fiber), and immobilized on the surface (S) of the solid conducting material. These conducting fibrillar organic species, objects of the invention, consist of a supramolecular association of triarylamines of formula (I) of the type of associations which were described in solution by the inventors in *Angew. Chem. Int. Ed.*, Vol. 49, pp. 6974-6978 (2010) which is incorporated herein by reference, these fibrillar supramolecular species being according to the present invention specifically grafted on the surface (S) of the solid conducting material at the end of step (E).

The present invention according to a second aspect relates to a conducting material or device comprising two conducting metal materials, the surfaces of which, (S) and (S') respectively, are electrically interconnected by an organic material comprising conducting fibrillar organic supramolecular species comprising an association of triarylamines of formula (I).

By "conductors", reference is made to electric conduction.

By "electrically interconnected" is meant the capability of having preferably a conductivity above $10^3$ S·m$^{-1}$, and generally from $10^4$ S·m$^{-1}$ to $10^5$ S·m$^{-1}$. The devices of the invention have current (I) values attaining the mA range. The conductance is generally of the order of a few tens of mS. According to a preferred embodiment, the devices of the invention advantageously have ohmic resistivity.

According to another aspect, the object of the present application is a method for preparing the aforementioned supramolecular species. This method includes a step in which a liquid medium containing triarylamines of formula (I) is subjected to electromagnetic radiation (typically solar radiation) or further to chemical or electrochemical oxidation, suitable for at least partly converting them into triarylammonium radicals, while subjecting them to an electric field typically from 200 to 600 mV, for example between 250 and 500 mV.

According to the method of the present invention, these fibrillar supramolecular species are specifically grafted onto surface (S) of the solid conducting material at the end of step (E). These supramolecular species typically have the shape of small fibers having a length of the order of 10 nm to 1,000 nm, notably between 50 and 1,000 nm and a diameter from 5 to 50 nm, for example from 10 to 50 nm. Considering the application of a potential difference between the surfaces (S) and (S') during step (E), these fibers are formed in a localized way between both surfaces and parallel to the electric field lines. Moreover, they are systematically grafted on the surface (S), which allows suppression of the formation of free fibrillar supramolecular species (i.e. non-bridging between the electrodes) after rinsing. Thus with this method, unlike present techniques, it is possible to achieve an extremely localized deposit of conducting organic compounds, exclusively in the area located between both surfaces. Unexpectedly, considering the techniques existing to this day for achieving this type of deposition, this accurate localization is further achieved directly without having to apply expensive or complicated means. Thus, generally, step (E) in a simple, efficient and inexpensive way (simply by introducing the compounds of formula (I) in solution between both surfaces (S) and (S'), by applying a simple potential difference between both of these surfaces and by subjecting the assembly to irradiation, typically with sunlight) gives the possibility of grafting organic fibrillar structures with electric conduction at the surface of a conducting solid.

According to a particularly interesting embodiment, step (E) is conducted with a sufficiently small distance between the surfaces (S) and (S') so that the fibrillar supramolecular associations formed on the surface (S) come into contact with the surface (S'). In this case, step (E) leads to an electric connection of the conducting surfaces (S) and (S'). Typically, in this case, the surfaces (S) and (S') facing each other are separated by 1 micron or less, or, at the very least, there exists at least one area of the surface (S) at a distance of 1 micron or less (for example from 10 to 1,000 nm) from an area of the surface (S'). Preferentially, when an electric connection of the surfaces (S) and (S') is sought, the latter are parallel or substantially parallel with a gap between both surfaces ranging preferably from 10 to 1,000 nm, for example from 50 to 500 nm.

According to a particular embodiment, said conducting material or device has a metal/organic interface and the surfaces (S) and (S') are separated by a distance of 10 to 500 nm, and preferably from 50 to 200 nm, in which said organic material comprising fibrillar organic supramolecular species fills the distance separating the surfaces (S) and (S') of both metal materials. Said distance is typically 80±20 nm. This is referred to as a <<nano-gap>>.

According to an alternative, the material or device of the invention has a length of the surfaces (S) and (S') facing each other comprised between 10 μm and 1,000 μm, and preferably from 50 to 500 μm. Said length is typically about 100 μm.

According to a preferred alternative, the fibrillar organic supramolecular species are oriented as a parallel bundle of <<nano-wires>> extending radially relatively to the conducting surfaces (S) and (S'), i.e. so that the greatest length of the fibrillar species joins said surfaces (S) and (S').

Fibrillar organic supramolecular species are preferred, for which the length corresponds to the distance separating the surfaces (S) and (S') of both metal materials.

Preferably, the metal materials are metal materials of conducting electrodes. As a material, preference is given to metals selected from transition metals and preferably from gold (Au) nickel (Ni), titanium (Ti), silver (Ag), iron (Fe), platinum (Pt), copper (Cu), cobalt (Co), zinc (Zn), chromium (Cr), manganese (Mn), or alloys comprising one or more of these metals. The electrodes may comprise an association of an electrode comprising or consisting of gold and nickel or of Nickel and iron, or of copper and gold, or of silver and gold, preferably with gold in surface of the electrode.

The present invention further relates to an interface between two metal electrodes comprising or consisting of fibrillar organic supramolecular species of the invention.

The invention also relates to the use of fibrillar organic supramolecular species comprising triarylamines fitting formula (I) in order to connect together the surfaces (S) and (S') of two conducting electrodes. The electrodes may be the aforementioned metal electrodes.

Preferably, at least one electrode comprises a transition metal, and preferably the whole of the electrodes used (for example the positive electrode and the negative electrode).

According to an alternative, the conducting metal of at least one electrode is covered with a gold (Au) deposit. Preferably, the whole of the electrodes used comprise a gold deposit (for example the positive electrode and the negative electrode).

In the particular case when step (E) is used for making the electric connection of the surfaces (S) and (S') according to the specific embodiment described above, this leads, as this is systematically the case in step (E), to the formation of fibrillar supramolecular species in an exclusively localized way within the space comprised between both surfaces, without any risk of depositing conducting organic compounds in other areas. The method consequently proves to be particularly selective and targeted, unlike most techniques applying organic compounds for connecting two conducting elements. Further, the fibrillar supramolecular species which are formed, are oriented by themselves parallel to the lines of the applied electric field between the surfaces (S) and (S'), i.e. along a parallel bundle of <<nanowires>> extending radially relatively to the conducting surfaces (S) and (S'), which is the optimum conformation for ensuring maximum electric connection between both surfaces. Further, the connection is effected rapidly, with response times at most of the order of one second.

In addition to this particularly favorable conformation, it is further found that unexpectedly, the fibrillar supramolecular species formed during step (E) are very good conductors, with a conductivity of the order of that of the best organic conductors known today (typically of the order of several tens of kiloSiemens per meter) and further with a behavior of ohmic conductors, unlike most conducting polymers. In other words, the supramolecular species schematically behave like metal nano-wires, notably with a resistance which decreases with temperature (notably in the range between 4 and 298 K). In a particularly surprising way, this effect is obtained within the scope of the present invention with species which are purely organic, without requiring application of additional metal cations which are conventionally used as dopants in many conducting organic polymers. With this possibility of doing without the application of metal compounds, it is possible to avoid the associated drawbacks in terms of toxicity and repercussion on the environment, which further is a particularly interesting aspect of the method of the invention.

Further, in still a more unexpected way, the inventors have brought to light within the scope of the present invention that the fibrillar supramolecular species which are produced in step (E), lead to particularly low contact resistances at the contact with the surfaces (S) and (S'). Indeed, the obtained contact resistance may be as low as of the order of $10^{-2}$ $\Omega \cdot cm$ in most of the cases, versus contact resistances which are at the very least of the order of 10 k$\Omega \cdot cm$ with most molecules recommended in the state of the art.

Moreover it should be emphasized that, unlike most organic compounds used as electric conductors, the fibrillar supramolecular species which are made in step (E) lead to good results in terms of conductivity, notably when the conducting materials present at the surfaces (S) and (S') comprises gold. Good results are further generally obtained regardless of the nature of the conducting material present at the surfaces (S) and (S'), which allows the method to be particularly modular.

Thus, it is found that step (E) in an extremely simple and direct way allows an efficient electric connection to be made between conducting objects separated from each other by a few tens to a few hundred nanometers, and this regardless of their exact physico-chemical nature. Unexpectedly, this particularly effective electric connection is obtained by simple self-association of the compounds of formula (I) during step (E), without having to apply complicated or expensive techniques. The fibrillar supramolecular species made in step (E) consequently are an extremely interesting alternative to organic compounds such as oriented conjugate polymers which are by far much more complicated to synthesize.

In addition to these different advantages, the inventors have further shown within the scope of the present invention that the fibrillar supramolecular species deposited on the surface (S) are stable at room temperature and they are even more stable, including at a higher temperature, once the solvent used in step (E) has been removed for forming these species. Consequently, most often in the method of the invention, step (E) is followed by a step (E') for removing the solvent used in step (E), which may typically be achieved by simple rinsing. By applying this step (E'), it is possible to stabilize the fibrillar supramolecular species attached on the surfaces (S) and optionally (S'), these species generally remaining stable and secured to the surface (S), and to the surface (S') if required, even when they are brought to temperatures of the order of 100° C. With this step (E'), it is also possible to remove possible compounds which are not engaged in the formation of the supramolecular species bound to the surface (S).

It should be noted that in the presence of a solvent, on the contrary, the fibrillar supramolecular species tend to disassemble at a high temperature, in particular at a temperature in the order of 100° C., in order to lead to the formation of a solution comprising the compounds (I) in a solubilized form. This specificity makes the formation of the fibrillar supramolecular species of step (E) reversible. Thus, if need be, an electric connection as obtained at the end of step (E) may very simply be broken by bringing the medium to a temperature of the order of 100° C., if the solvent has not been removed. With this possibility it is for example possible to correct possible connection errors during the manufacturing of electric or electronic circuits. If step (E') has been applied, it is still possible to consider such a reversibility. In order to disassemble the fibrillar supramolecular species, it is then sufficient to put these species back in the presence of a solvent, and then to raise the temperature of the medium to 100° C. The reversibility of the method further is one of its numerous assets, making it most particularly suitable for an industrial application. This reversibility of the formation of the fibrillar supramolecular species from compounds of formula (I) allows them to be considered for making memories.

Different advantages, features, and preferential embodiments of the invention will now be described in more detail.

Triarylamines of Formula (I)

Preferably, the triarylamines of formula (I) used in step (E) are a population of identical molecules. However, according to certain embodiments, the use of a mixture of several distinct triarylamines is not excluded.

According to an embodiment well adapted to the application of the present invention, the triarylamines of formula (I) used in step (E) are compounds wherein each of the groups -A$^1$- and -A$^2$- is a group —O—.

Moreover, it proves to be generally of interest that in the triarylamines of formula (I) used in step (E), each of the groups R$^1$ and R$^2$ independently represents:
- a benzyl group; or
- an advantageously linear alkyl group typically comprising from 6 to 18 carbon atoms, preferably from 7 to 10 carbon atoms.

Thus, according to an interesting embodiment, the triarylamines of formula (I) used in step (E) may for example fit the formula (1a) below:

wherein:
- each of the groups R$^1$ and R$^2$, either identical or different (and preferably identical) have one of the aforementioned meanings and preferably designates a benzyl group or else an advantageously linear alkyl group, comprising from 6 to 18, for example 7 to 10, and notably 8 carbon atoms;
- A is a hydrogen group —H; a halogen group, for example a group —Cl; or else an alkyl group typically comprising from 1 to 8 carbon atoms (for example, 5, 6, or 7 carbon atoms).

Triarylamines adapted to the application of the invention notably include, in a non-limiting way, the compounds fitting formula (Ia) above, wherein R$^1$, R$^2$, and A have one of the following meanings:
- R$^1$=R$^2$=C$_8$H$_{17}$ (linear) and A=Cl; or
- R$^1$=R$^2$=C$_8$H$_{17}$ (linear) and A=H; or
- R$^1$=R$^2$=C$_8$H$_{17}$ (linear) and A=C$_6$H$_{13}$; or
- R$^1$=R$^2$=benzyl and A=H; or
- R$^1$=R$^2$=benzyl and A=Cl.

A method for preparing these compounds was notably described in *Angew. Chem. Int. Ed.*, Vol. 49, pp. 6974-6978 (2010).

Regardless of the exact nature of the triarylamines applied in step (E), the latter are applied within a solvent. This solvent may be selected from all the solvents capable of solubilizing the compounds of formula (I) used in step (E). Well-adapted solvents within this scope are chlorinated solvents, such as chloroform, dichloromethane or further still 1,1,2,2-tetrachloroethane.

The step (E') for removing this solvent may typically be carried out by using one of these same chlorinated solvents as a rinsing solvent.

Triarylamines are generally applied in step (E) as solutions having concentrations of the order of 1 to 100 mmol/L, preferably between 5 and 20 mmol/L. Such solutions are liquid compositions at room temperature and clearly less viscous than the usual compositions of conducting organic polymers known from the state of the art, this low viscosity allowing improvement in the control and handling as compared with the methods using this type of polymers, this further is a non-negligible advantage of the method of the invention.

The Potential Difference Applied in Step (E)

In the method of the invention, a potential difference is applied between the surface (S) and the surface (S'), so as to induce an electric field in the space located between both of these surfaces. Generally, this potential difference is negative, so as to induce grafting of the fibrillar supramolecular species at least on the surface (S).

The absolute value of this potential difference should be sufficient in order to induce the sought effect, but however it should not be too high so as not to lead to too low conductivities. The value of the potential difference should moreover be adapted to the distance between the surfaces (S) and (S'). As an indication, for a distance between the surfaces (S) and (S') of the order of 80 to 100 nm, for example the absolute value of the potential difference applied during step (E) between the surfaces (S) and (S') is preferably of the order of 10 to 700 mV, more preferentially from 50 to 500 mV, for example between 100 and 400 mV, notably between 200 and 400 mV.

For the same gap between the surfaces (S) and (S'), in the particular case of the use of the compounds of the aforementioned formula (Ia), and most particularly in the case of the compound of formula (Ia) wherein R$^1$=R$^2$=C$_8$H$_{17}$ and A=Cl, the absolute value of the potential difference applied during step (E) between the surfaces (S) and (S') is preferably comprised between 250 and 350 mV, typically of the order of 300 mV.

Establishment of the potential difference may be accomplished according to any means known per se, the simplest being to connect the surfaces (S) and (S') to the terminals of an electric generator delivering the sought voltage.

According to an alternative, application of the potential difference begins before putting the surfaces (S) and (S') of the solid conducting materials in contact with the solution comprising the triarylamines. According to another alternative, application of the potential difference begins after this contacting. According to another alternative, application of the potential difference begins at the moment of this contacting.

According to a preferred alternative, an initial potential difference of at least 0.1V and preferably of at least 0.3V is applied between the electrodes, before light irradiation.

The Electromagnetic Radiation Applied in Step (E)

During step (E), the compounds of formula (I) are subject to irradiation by electromagnetic radiation capable of activating them, i.e. at least partly converting them into triarylammonium radicals.

The radiation used for this purpose contains at least wavelengths with an energy with which the sought conversion may be achieved. For a given compound of formula (I), this wavelength is very easy to determine since it generally corresponds to the absorption peak $\lambda_{max}$ of the compound on a UV-visible light absorption spectrum.

For example, for the compound of formula (Ia) wherein $R^1=R^2=C_8H_{17}$ and A=Cl, the effective wavelength is located around 350-365 nm.

Generally, the useful wavelength for activating a given compound of formula (I) is part of the spectrum of sunlight. Consequently, the irradiation of step (E) may advantageously be carried out according to a particular embodiment by subjecting the medium of step (E) to solar radiation. This particularly simple and inexpensive embodiment makes the method very easy to carry out.

Alternatively, step (E) may be conducted by using only one portion of the solar spectrum. In this case the wavelengths used advantageously comprise at least the wavelengths comprised between $\lambda_{max}-25$ nm and $\lambda_{max}+25$ nm, more preferentially at least the wavelengths comprised between $\lambda_{max}-50$ nm and $\lambda_{max}+50$ nm.

As regards the irradiation, it should be noted that its power has an effect on the formation of the fibrillar supramolecular species based on compounds (I). As a general rule, these species form all the more rapidly as the power is high. Nevertheless, too high irradiation powers should be avoided since they are capable of leading to parasitic phenomena such as the induction of a radical polymerization reaction. As an indication, in particular for the aforementioned compounds of formula (Ia), a power of the order of 100 W is suitable (for example between 50 and 200 W, i.e. powers of the order of 10 W·cm$^{-2}$ based on the distance but which may be lower and at least as low as 0.01 W·cm$^{-2}$ according to the applied irradiation time), while powers of 1,000 W are detrimental to the quality of the obtained result.

The irradiation may be replaced with a chemical oxidation step, for example by using an oxidant such as DDQ (dichlorodicyanoquinone) in catalytic amounts (typically 1%). It is also possible to form radicals which are initiators of fibrillar self-assembling, electrochemically by oxidizing the triarylamine derivative.

Regardless of the applied embodiment, conducting the steps (E) and (E') of the present invention is very simple and inexpensive. In addition to the aforementioned advantages, it should further be emphasized on this subject that these steps may advantageously be conducted at room temperature.

Because of its ease of application and of its great modularity, the method of the invention lends itself to a large variety of applications.

In particular, the steps (E) and (E') may be used for connecting together two electric conductors, for example two constituents of an electronic circuit. Within this scope, the method of the invention may be used at any scale, including miniaturized or even nanometric circuits.

A particular application of the method of the invention relates to the repair of electronic circuits interrupted locally. Within the scope, the steps (E) and (E') may be used for locally carrying out the equivalent of a "weld" on a damaged portion of the electronic circuit, by reconnecting the interrupted circuit by means of the fibrillar supramolecular species. In this case, the surfaces (S) and (S') may for example be both lips on either side of a break or of a damaged area having led to a loss of conduction.

More generally, the method of the invention may be used for any deposition of fibrillar supramolecular species of the aforementioned type on a conducting surface, in an organized form, i.e. bound to the surface and extending radially relatively to this surface.

Within this scope, the relatively rapid response of the system gives the possibility of contemplating <<writing>> on a conducting surface, by moving parallel to this surface, a surface (S') of a smaller size, this surface (S') then playing the role of a tip (printing head) defining a pattern upon moving over the conducting surface. This embodiment may for example be used for optically writing conducting tracks based on fibrillar supramolecular species on a conducting support. Such conducting tracks allow conduction of the metal type while further having the advantage of being mechanically flexible unlike metal tracks.

According to another aspect, the object of the present invention is conducting materials modified at the surface by fibrillar supramolecular species based on triarylamines of formula (I), of the type of those obtained at the end of step (E) and of the optional step (E') defined above.

Within this scope, the object of the present invention is materials which are practically obtained according to steps (E) and optionally (E') but also all materials having the same characteristics but obtained according to another method leading to the same result.

In particular, the invention encompasses conducting materials which bear at the surface fibrillar supramolecular species based on triarylamines of formula (I) which are obtained not by using irradiation, but by using an oxidizing agent in order to induce conversion of the triarylamines of formula (I) into triarylammonium radicals.

The invention also relates to conducting materials which bear at the surface fibrillar supramolecular species based on triarylamines of formula (I) which are obtained by treating a conducting material via an electrochemical route in the presence of triarylamines of formula (I).

The materials of the invention may be applied in parallel with a so-called downward moving technique or <<top-down>> approach such as inkjet printing, preferably with a high resolution or a lithographic method optionally using patterns induced by light.

The invention also allows applications for welds of electronic or bioelectronic circuits and therefore only relates to such methods.

The present invention and its advantages will still be further illustrated considering the example hereafter.

In the figures:

FIG. 1 illustrates a schematic view of the geometry of a nano-gap associated with a typical conductance measurement and with atomic force microscopy (AFM) images. (A) in particular represents a solution of compounds of the invention drop-casted in the dark, on nano-patterned Au/Ni electrodes. The applied potential difference between both electrodes is comprised between 0.3 and 0.8V. The measured conductance for the interconnection without the structures of the invention is of the order of one picosiemens. The sample is then subjected to light, which produces radicals inducing the supramolecular structures of the invention by live radical polymerization resulting in aligned self-assembling along the electric field and strong connection of both electrodes. (B): topography of the open gap (on the left) as seen with AFM before irradiation and after irradiation, filled with the supramolecular structures of the invention (on the right). (C): an AFM image before radiation showing a nano-gap (surface scale 1500×1500 nm$^2$). (D) an AFM image after irradiation (surface scale 1500×1500 nm$^2$): the nano-gap filled with nano-wires or nano-filaments is seen. (E) Zoom on the nano-gap filled with nano-wires (surface scale 250×250 nm$^2$).

wherein $k_B$ is Boltzmann's constant and wherein $\hbar\omega_0$ is the energy of the photons.

EXAMPLE 1

A connection of two electrodes was achieved according to the method of the invention, by using a device of the type of the one described in *Nanotechnology*, 21, 335303 (2010), which has two electrodes facing each other.

To do this, a compound fitting the aforementioned formula (Ia), wherein $R^1=R^2=C_8H_{17}$ (linear) and A=Cl, was used, dissolved in an amount of 10 mmol/L in chloroform.

The solution of the compound was placed in the gap between two electrodes and then the device was irradiated with white light with a power of 100 W, while imposing a potential difference of 300 mV between the electrodes.

The very rapid formation of an electric connection between both electrodes was then observed, which is expressed by a measurement of the conductivity between both electrodes: before the treatment, a current is measured of the order of a few picoamperes between both electrodes, versus a current of 0.5 A (i.e. $10^8$ fold increase) after the treatment.

Micrographs reveal the presence of fibrillar supramolecular species which ensure the electric connection between the electrodes, organized in parallel and extending perpendicularly to the surface of the electrodes.

EXAMPLE 2

Figure 1:
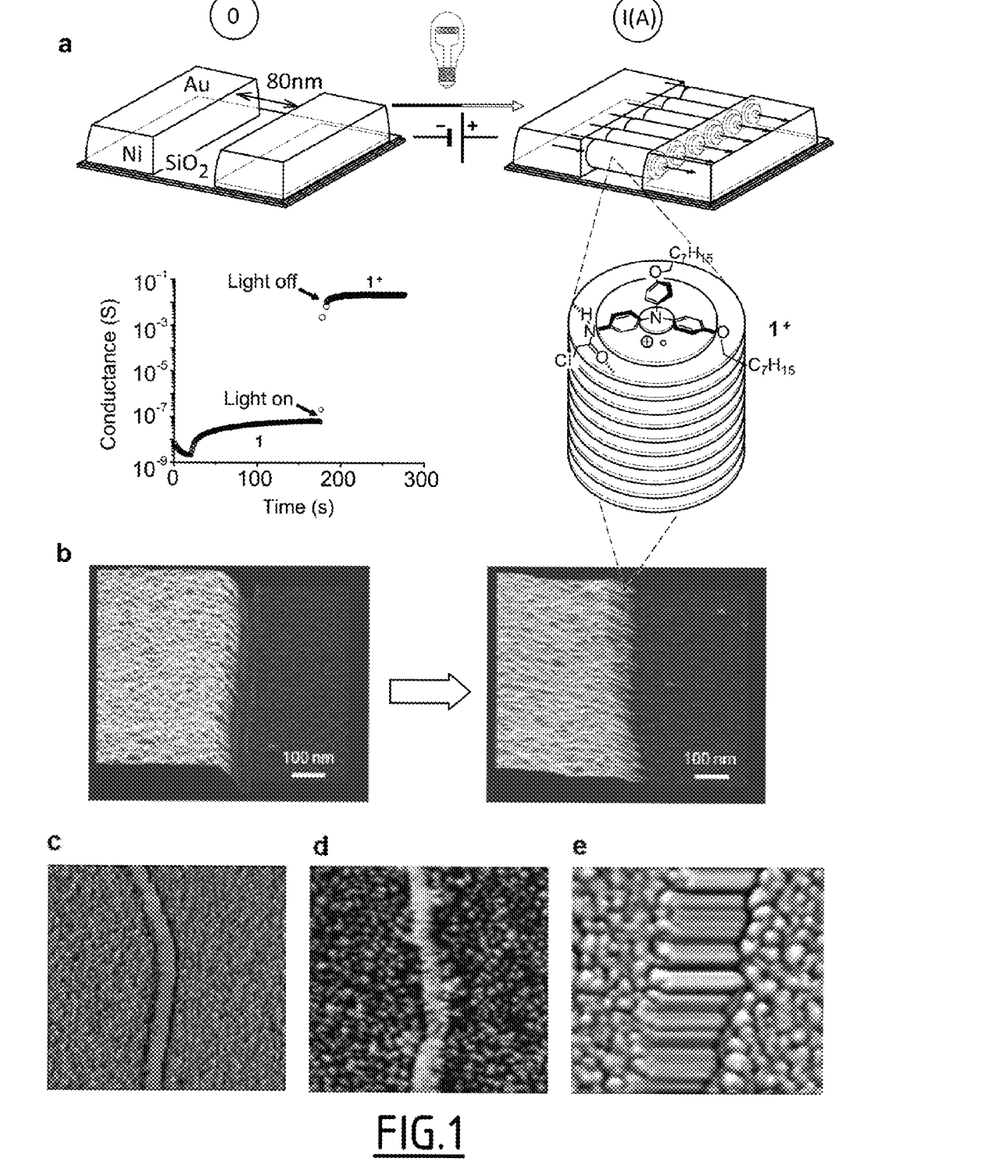
Figure 2:
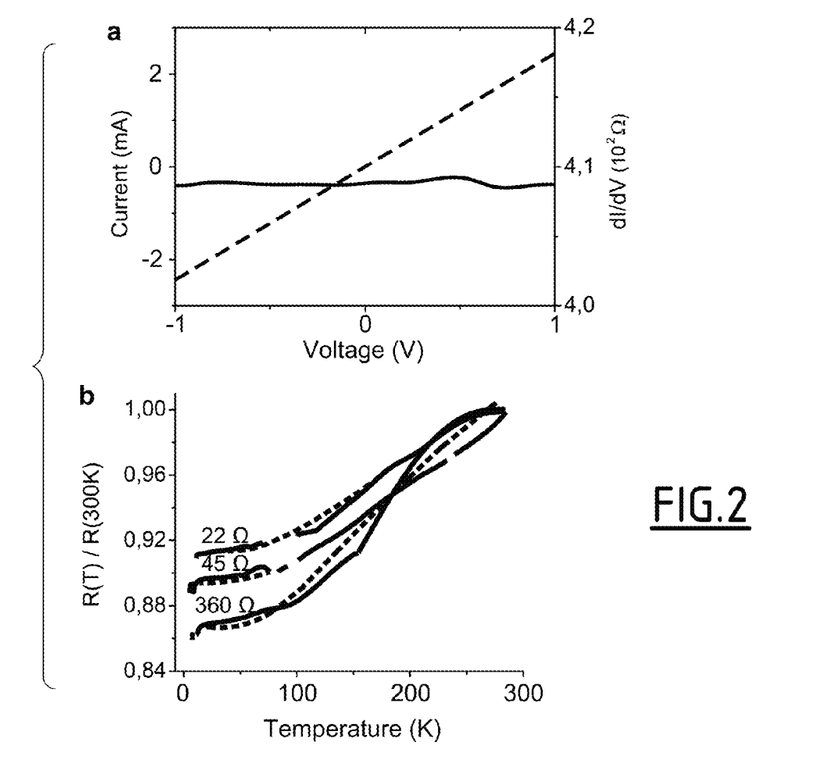
FIG. 2 represents the ohmic behavior and conductivity characteristics of the supramolecular structures versus temperature: (A) current versus voltage curve, measured at a low temperature (1.5K). (B) normalized R(T) measurement of three devices functionalized by supramolecular structures of the invention, between room temperature and 1.5K. The initial resistances for each sample at 300K are the following: 22, 45 and 360Ω. Each sample is correlated by using the equation $$\frac{1}{R}(T) = \frac{1}{R_0} \cdot \exp\left(\frac{\hbar\omega_0}{k_B T}\right)$$

By an optical lithography technique on a silicon substrate, Au and Ni electrodes were made, the surfaces of the electrodes being separated by a distance of about 80±20 nm, over a width of 100 µm. The residual current is less than 1 pA between both surfaces. This circuit is immersed in a solution of molecules of formula (Ia) and in particular of molecules of formula (Ia), wherein $R^1=R^2=C_8H_{17}$ (linear) and A=Cl, in 1,1,2,2-tetrachloroethane ($C_2H_2Cl_4$) (FIG. 1A), in the absence of light. An increase in the current between the electrodes by a few hundred pA was observed under a differential voltage of a few hundred mV (see FIG. 4). Following irradiation, using white light, a six fold increase in the current is observed, thereby attaining values in the mA range. The corresponding conductance is of a few tens of mS. These devices with 2 terminals with channels and interfaces of series contacts have an ohmic resistive behavior related to high conductivity values as shown by the measurement of the intensity versus the voltage I(V) (according to FIGS. 2A and 4). The conductivity of the channel is estimated as ranging beyond $10^4$ S·m$^{-1}$. Alternatively, it is estimated that the interface resistance per unit length is equal to or greater than $10^{-4}$ Ω·m. This value is of the order of six times less than that of the best contacts of simple organic crystals and less than what is obtained with graphene flakes.

After intense washing of the samples with the solvent, Atomic Force Microscopy (AFM) imaging reveals a length of <<nano-wires>> of conducting organic supramolecular structures exactly in line with the distance between the electrode surfaces (FIGS. 1B-E), with orientations along the electric field applied to the assembly and with a homogeneous diameter of 12±2 nm. It was discovered that it is important to apply an initial threshold voltage (of at least 0.1V and preferably at least 0.3V?) between the electrodes, before light irradiation, in order to effectively obtain in a stable way the fibrillar supramolecular structures.

It was also observed that the method for preparing these structures may be reversible when the sample is heated for example to 60° C. overnight, since the formed supramolecular structures dissolve. After repeated assemblings and disassemblings (six times), the metal interconnections were not significantly effected by the heating cycles.

After evaporation of the solvent, the obtained structures become stable and provide reproducible results after one night of heating at 100° C. The performances of the samples are not notably sensitive to humidity nor to oxygen which is highly positive for organic electronic devices. It was not necessary to operate under inert atmosphere conditions during the preparation of the supramolecular structures. After one month of storage, the samples exhibited comparable conducting properties.

Figure 4:
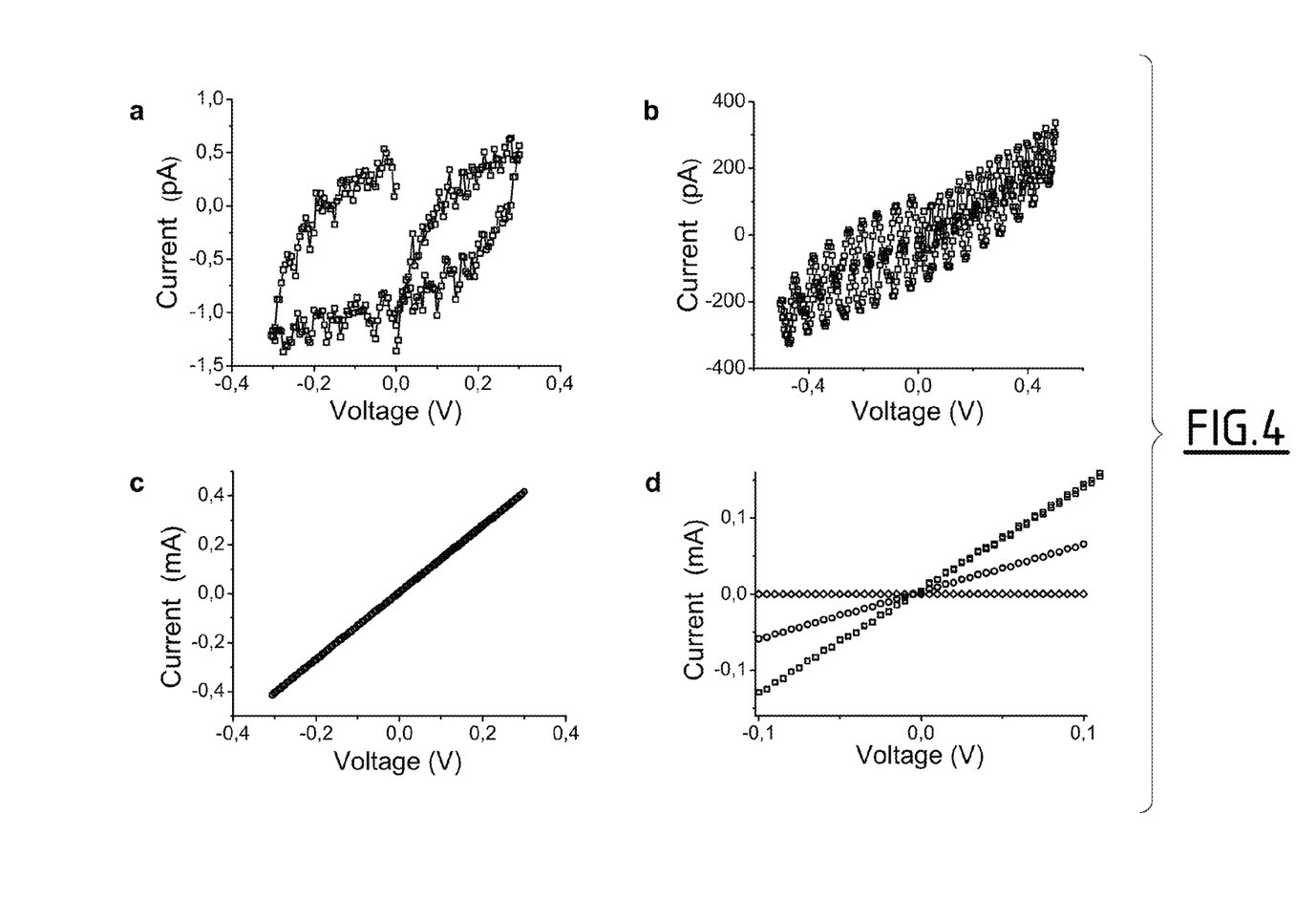
FIG. 4 illustrates the current versus voltage I(V) measurements: (A) (IV) of an empty nano-gap (width 100 µm, length 0.08 µm). (B) I(V) of a reference nano-gap immersed in a solution of the compounds of the invention, before light irradiation. The residual current is ascribed to ion impurities in the solution. (C) I(V) of a nano-gap after self-assembly of the compounds of the invention under light irradiation. (D) I(V) of a nano-gap showing the effect of the applied voltage during the initial light irradiation (diamonds: 0.01 V, circles 0.1 V, squares: 0.3 V).

Studies versus temperature confirmed that the samples had high conductivity since they systematically and reliably reveal resistivity decreasing with temperature, down to 1.5K (FIG. 2B). The ohmic profile of the structures was also noted up to high currents at low temperature (FIG. 2A). For the samples exhibiting the smallest resistance, currents up to 25 mA were observed when they are subject to a potential difference of 1V in vacuo (FIG. 4B). The current density is estimated to be of the order of $10^7$ A·cm$^{-2}$, which is remarkably high for organic compounds and corresponds to electromigration density currents in the metal circuits.

EXAMPLE 3

Samples were also made with analogs of compounds of Example 1. In a blind test configuration, it was noticed that the inter-electrode gap was only filled with supramolecular structures when they are capable of self-assembling. This confirms that the conducting properties result from the supramolecular structures of the invention. The following compounds were tested.

TABLE 1

| Molecule | Behavior in solution Determined by $^1$H NMR (1) | State of the gap |
|---|---|---|
|  1 | Self-assembled | Closed |
|  2 | Self-assembled | Closed |
|  3 | Self-assembled | Closed |
|  4 | Non self-assembled | Open |

TABLE 1-continued

| Molecule | Behavior in solution Determined by $^1$H NMR (1) | State of the gap |
|---|---|---|
| 5 (triarylamine with OH, OH, and NHC(O)CH$_2$Cl substituents) | Non self-assembled | Open |
| 6 (triarylamine with OCH$_3$, OCH$_3$, and NHC(O)CH$_2$Cl substituents) | Non self-assembled | Closed (a) | a: The gap was however opened after rinsing with solvent under conditions where STANWs derivatives 1-3 remain stable; this shows the weakened mechanical properties of STAWNs starting from compound 6.

With $^1$H NMR, it was determined that the compounds 1-3 self-assemble in solutions of CDCl$_3$ after light stimulation, which is not the case of the compounds 4-6. This property related to the structure shows that only the compounds of the invention have the capability of self-assembling.

The experimentation was carried out by blind tests. The person having prepared the solutions did not carry out the conductivity measurements. The samples were coded. Each sample was measured under the same conditions: the 1V potential difference was applied on the solution of triarylamines 1-6 (1 mg·mL$^{-1}$), simultaneously with an irradiation of 100 W at a constant distance for a period of 10 seconds ($\approx$10 W·cm$^{-2}$); and then the I/V dependency was measured for each distance. The results are summarized in Table 1. The correlations clearly show that the conductivity is dependent on self-assembly.

Images of the Nano-Gaps.

The morphology and the difference between the electrodes before and after self-assembly were observed, for this, a scanning electron microscope (SEM) was used and an atomic force microscope (AFM) was used for obtaining qualitative and quantitative information on the nano-gaps.

The images taken with AFM (FIGS. 1C, D and E) give a specific indication of the fibrillar structure of the filled nano-gaps.

EXAMPLE 4

Figure 3:
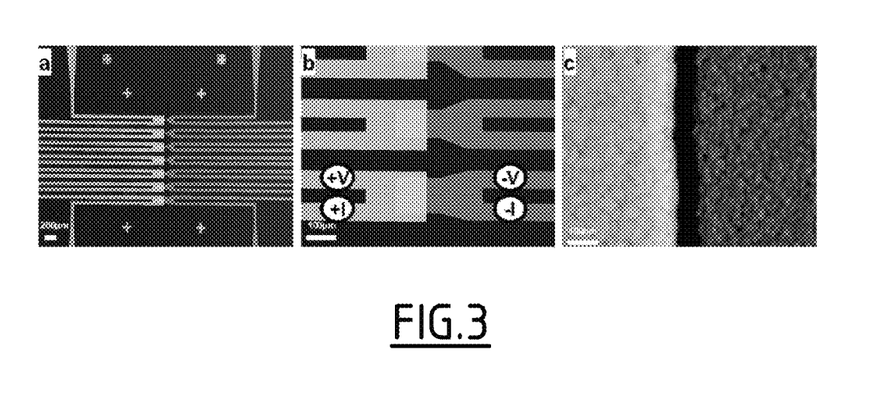
FIG. 3 illustrates a design of electrodes: (A) a nano-gap of electrodes observed under a scanning electron microscope (SEM). (B) A zoom illustrating four pseudo-connection points, limiting the series resistance of the interconnections to below 2Ω. (C) A zoom on the nano-gap illustrating a typical distance of less than 100 nm.

Electrodes were made with edge mediated shadow mask lithography according to the technology described in J-F Dayen et al; Nanotrench for nano and microparticle electrical interconnects; Nanotechnology 21 335303 (2010)—a triple layer Ti(5 nm)/Ni(35 nm)/Au(20 nm) was first deposited by electron beam evaporation, followed by a standard lift-off method. The second step comprises the deposition under an angle of 60°, by creating a triple layer Ti(5 nm)/Ni(25 nm)/Au(10 nm) followed by a lift-off. The first electrode has a composition related to the superposition of two steps, and the second thinner electrode, has a composition only corresponding to the second layer of the deposited triple layer (this explains the height difference observed with AFM). The <<nano-gaps>> were made with a fixed inter-electrode distance of 80 nm and a length of 100 μm (FIG. 3). After checking the absence of any residual current, a solution of the compound formula (Ia), wherein $R^1=R^2=C_8H_{17}$ (linear) and A=Cl (at 1 mg/mL in $C^2H^2Cl^4$), were deposited by drop casting on the electrodes. A potential difference of more than 0.3V and up to 0.8V with a DC current, was immediately applied between the electrodes, the time-dependent change in the current was recorded by using a measurement instrument with high resistances (electrometers) of the Keithley 6517B Electrometer/High Resistance Meter type. The sample was irradiated for a few seconds under illumination through a microscope condenser (numerical aperture of 0.55) with a 100 W halogen light source. An infrared filter was used for limiting the heating of the sample to a few degrees, which results in irradiation with a wide band power density of 10 W·cm$^{-2}$. The typical irradiation time of 10 s corresponds to the total number of photons used in about 30 minutes for achieving self-assembly in solution by using a power density of about 0.07 W·cm$^{-2}$, which is more than required for generating self-assembly. It was also discovered that a transition metal in the electrode was necessary for ensuring more satisfactory interconnection of the self-assembly. It is not possible to obtain stable and reliable self-assembly only between Au and Pt electrodes (with a Ti adhesion layer). The self-assembly has a success rate of more than 90% between two Ni and Fe electrodes. It was discovered that use of a gold deposit (Au) on the electrodes provides better long term stability of the samples, and with this it is possible to overcome the problem of surface oxidation of the transition metals.

On the other hand, an effect initiating the growth of the self-assembly was observed with a substrate of the transition metal type.

After the formation of the supramolecular structures, the samples were rinsed with chloroform, followed by intensive washing with acetone and ethanol, and then finally dried with a stream of nitrogen.

Low temperature electric measurements were conducted with a cryostat having a vacuum pump ($P<10^{-6}$ mbar) or in a helium (He) flow system lowering the temperature to 1.5K. The measurements of the electric properties were conducted with an Agilent E5270B semiconductor parameter analyzer (DC properties), and with an SRS 830 lock-in amplifier (AC properties).

Figure 5:
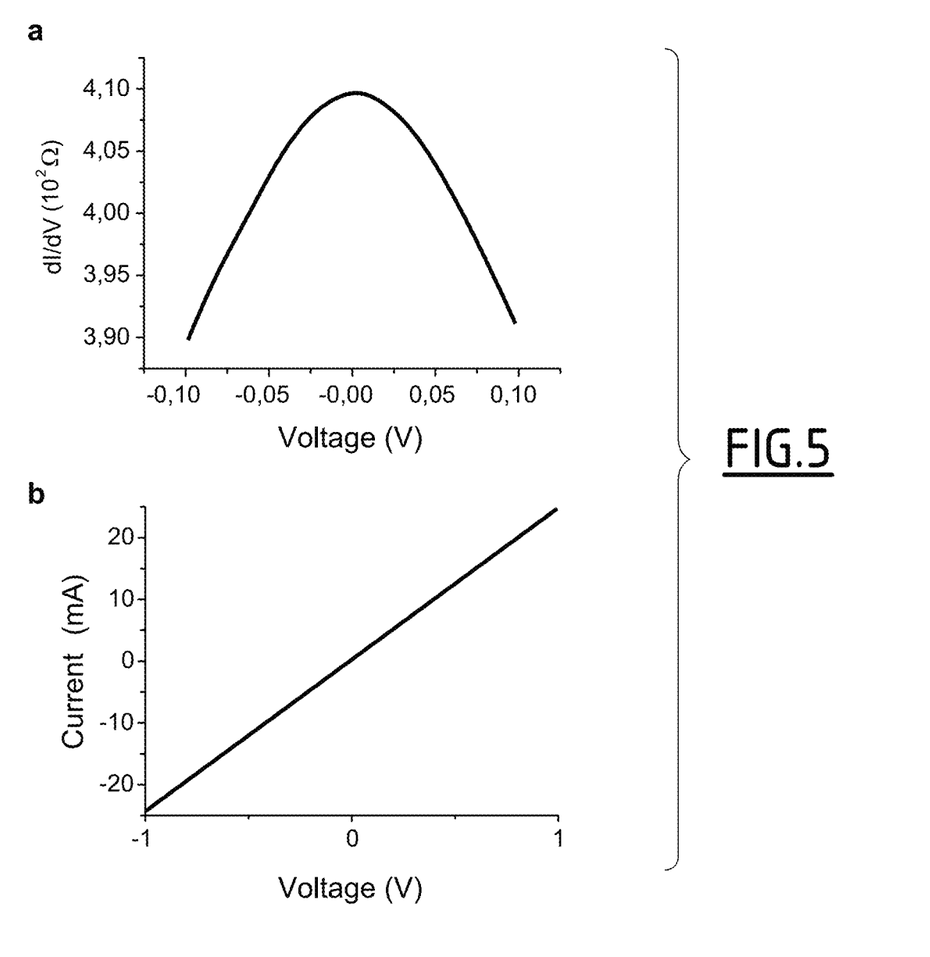
FIG. 5 represents the differential conductance measured at 200K in vacuo by using the AC bridge technique. (A) reduction of the conductance with the potential difference indicating possible heating of the samples in solution. (B) an integrated curve illustrating current values of a few tens of mA at higher potential differences.

Differential conductance measurements were also conducted at 200K in vacuo. A current with an intensity of a few tens of mA was observed in a reproducible way with a 1V potential difference applied on different samples (FIG. 5).

The invention claimed is:

1. A method for preparing fibrillar supramolecular species comprising triarylamines of formula (I) below:

wherein:
each of the groups -$A^1$- and -$A^2$-, either identical or different designates a covalent bond or a group —O—, —S—, —NH—, —NH(C=O)—, or —$NR^3$—;
each of the groups $R^1$, $R^2$ and $R^3$, either identical or different, represents:
an aromatic group; or
a hydrocarbon chain comprising from 4 to 30 carbon atoms, optionally halogenated and optionally interrupted with one or more heteroatoms selected from N, O or S; or
a polyethylene glycol chain;
and
R is a terminating group;
said method comprising:
(i) preparing a liquid medium containing said triarylamines of formula (I);
(ii) subjecting said liquid medium containing said triarylamines of formula (I) to an electric field and irradiating said liquid medium containing said triarylamines of formula (I) with an electromagnetic radiation; and
(iii) obtaining said fibrillar supramolecular species comprising triarylamines of formula (I).

2. The method of claim 1, wherein said liquid medium comprises a chlorinated solvent.

3. The method of claim 1, wherein said fibrillar supramolecular species comprising triarylamines of formula (I) are formed and immobilized on a surface (S) of a solid conducting material.

4. The method of claim 1, wherein said fibrillar supramolecular species comprising triarylamines of formula (I) are electrically connecting two conducting solid elements.

5. The method of claim 1, wherein said method comprises:
grafting on a surface (S) of a solid conducting material said fibrillar supramolecular species comprising triarylamines of formula (I); and
connecting surface (S) and a surface (S') of another conducting solid placed facing the surface (S) with said fibrillar supramolecular species comprising triarylamines of formula (I).

6. The method according to claim 1, wherein the liquid medium comprises a solvent of said triarylamines of formula (I) and wherein said solvent is removed.

7. The method according to claim 1, wherein the wavelength of said radiation corresponds to the absorption peak $\lambda_{max}$ of the triarylamines of formula (I) on a UV-visible light absorption spectrum.

8. The method of claim 1, wherein each of the groups -$A^1$- and -$A^2$- represent —NH(C=O)—.

9. The method of claim 1, wherein each of the groups -$A^1$- and -$A^2$- represent a group —O—.

10. The method of claim 1, wherein each of the groups $R^1$ and $R^2$, represents, independently:
a benzyl group; or
an alkyl group comprising from 6 to 18 carbon atoms.

11. The method of claim 1, wherein the triarylamines fit the formula (Ia) below:

wherein:
each of the groups $R^1$ and $R^2$, either identical or different, designates a benzyl group or a linear alkyl group, comprising from 6 to 18 carbon atoms; and
A is a hydrogen group: a halogen group, or an alkyl group.

12. The method of claim 11, wherein $R^1$, $R^2$, and A have one of the following meanings:
$R^1$=$R^2$=$C_8H_{17}$ (linear) and A=Cl; or
$R^1$=$R^2$=$C_8H_{17}$ (linear) and A=H; or
$R^1$=$R^2$=$C_8H_{17}$ (linear) and A=$C_6H_{13}$; or $R^1=R^2$=benzyl and A=H; or
$R^1=R^2$=benzyl and A=Cl.

13. The method of claim 11, wherein each of the groups $R^1$ and $R^2$ independently represents a linear alkyl group comprising from 4-7 to 10 carbon atoms.

14. The method of claim 1, wherein each of the groups $R^1$ and $R^2$, either identical or different, designates a linear alkyl group comprising from 7 to 10 carbon atoms or a benzyl group.

15. The method of claim 1, wherein R is $CH_2$-A and A is a hydrogen group; a halogen group; or an alkyl group comprising from 4 to 30 carbon atoms.

16. The method of claim 1, wherein each of the groups $R^1$ and $R^2$ independently represents a linear alkyl group comprising from 4 to 30 carbon atoms.

17. The method of claim 1, wherein each of the groups -$A^1$- and -$A^2$-designates a group —NH(C=O)—; and wherein each of the groups $R^1$, and $R^2$, either identical or different, represents a hydrocarbon chain comprising from 4 to 30 carbon atoms, optionally halogenated and optionally interrupted with one or more heteroatoms selected from N, O or S.

18. The method of claim 1, wherein said fibrillar supramolecular species comprising triarylamines of formula (I) form nano-wires or nano-filaments.

19. A method for modifying a surface (S) of a solid conducting material, wherein said method comprises:
  positioning a surface (S) of a solid conducting material and a surface (S') of another conducting solid material so that surface (S') is facing said surface (S);
  putting said surface (S) in contact with a liquid medium comprising in solution at least triarylamines of formula (I);
  applying a potential difference between said surface (S) and said surface (S'), and
  subjecting said liquid medium comprising in solution at least triarylamines of formula (I) to an electromagnetic radiation or to chemical or electrochemical oxidation to produce triarylammonium radicals from said triarylamines;
  wherein said triarylamines of formula (I) are as follows:

(I)

wherein:
  each of the groups -$A^1$- and -$A^2$-, either identical or different designates a covalent bond or a group —O—, —S—, —NH—, —NH(C=O)—, or —$NR^3$—;
  each of the groups $R^1$, $R^2$ and $R^3$, either identical or different, represents:
  an aromatic group; or
  a hydrocarbon chain comprising from 4 to 30 carbon atoms, optionally halogenated and optionally interrupted with one or more heteroatoms selected from N, O or S; or
  a polyethylene glycol chain;
  and
  R is a terminating group; and
  forming fibrillar supramolecular species comprising triarylamines of formula (I) immobilized on said surface (S) of said solid conducting material.

20. The method according to claim 19, wherein said method comprises electrically connecting surfaces (S) and (S') where the surfaces (S) and (S') facing each other are distant from each other by 1 micron or less.

21. A method for a preparing or repairing an electronic or optoelectronic device, said method comprising:
  (i) preparing a liquid medium containing said triarylamines of formula (I) below:

(I)

wherein:
  each of the groups -$A^1$- and -$A^2$-, either identical or different designates a covalent bond or else a group —O—, —S—, —NH—, —NH(C=O)—, or —$NR^3$—;
  each of the groups $R^1$, $R^2$ and $R^3$, either identical or different, represents:
  an aromatic group; or
  a hydrocarbon chain comprising from 4 to 30 carbon atoms, optionally halogenated and optionally interrupted with one or more heteroatoms selected from N, O or S; or
  a polyethylene glycol chain;
  and
  R is a terminating group;
  (ii) providing a solid device comprising two conducting metal materials having surfaces (S) and (S') facing each other and made of at least one metal material;
  (iii) putting said solid conducting device into contact with said liquid medium containing said triarylamines of formula (I);
  (iv) subjecting said liquid medium containing said triarylamines of formula (I) to an electric field;
  (v) subjecting said liquid medium containing said triarylamines of formula (I) to an electromagnetic radiation while subjecting said liquid medium containing said triarylamindes of formula (I) to an electric field according to step (iv); and (vi) obtaining an electronic or optoelectronic device comprising two conducting metal materials, the surfaces of which, (S) and (S') respectively, are electrically interconnected by an organic material comprising electronic conducting fibrillar organic supramolecular species comprising an association of triarylamines of formula (I).

22. The method of claim 21, wherein said step (iv) begins before step (v) of subjecting said liquid medium containing said triarylamines of formula (I) to an electromagnetic radiation.

23. The method of claim 21, wherein said metal materials are selected from the group consisting of gold (Au), nickel (Ni), titanium (Ti), silver (Ag), iron (Fe), platinum (Pt), copper (Cu), cobalt (Co), zinc (Zn), chromium (Cr), manganese (Mn), or alloys comprising one or more of these metals.

24. The method of claim 21, wherein said metal materials are metal materials of conducting electrodes and wherein at least one electrode is covered with a gold (Au) deposit.

* * * * *